United States Patent [19]
Munson et al.

[11] Patent Number: 5,783,938
[45] Date of Patent: Jul. 21, 1998

[54] METHOD AND APPARATUS FOR THE QUANTITATIVE MEASUREMENT OF THE CORROSIVITY EFFECT OF RESIDUES PRESENT ON THE SURFACE OF ELECTRONIC CIRCUIT ASSEMBLIES

[75] Inventors: Terry L. Munson, Kokomo; Douglas O. Pauls, Sheridan, both of Ind.

[73] Assignee: Contamination Studies Laboratories, Inc., Kokomo, Ind.

[21] Appl. No.: 804,795

[22] Filed: Feb. 24, 1997

[51] Int. Cl.⁶ .............................. G01N 1/04; G01R 27/10
[52] U.S. Cl. .................. 324/71.2; 73/86; 73/864.33; 436/6
[58] Field of Search ..................... 73/86, 866, 865.9, 73/864.71, 864.33, 864.81; 324/693, 700, 719, 722, 71.1, 71.2, 71.5; 422/82.02; 436/6; 134/113

[56] References Cited

U.S. PATENT DOCUMENTS

| | | | |
|---|---|---|---|
| 4,101,828 | 7/1978 | Dehler | 324/71.2 X |
| 4,731,154 | 3/1988 | Hazlitt et al. | 156/626 |
| 4,913,179 | 4/1990 | Engel et al. | 134/113 |
| 4,996,160 | 2/1991 | Hazlitt et al. | 436/2 |
| 5,027,841 | 7/1991 | Breunsbach et al. | 134/95 |
| 5,234,506 | 8/1993 | Winston et al. | 134/40 |
| 5,246,023 | 9/1993 | Breunsbach et al. | 134/57 |
| 5,296,041 | 3/1994 | Vinci et al. | 134/40 |
| 5,312,562 | 5/1994 | Vinci et al. | 252/174.14 |
| 5,396,178 | 3/1995 | Rybarski | 324/439 |
| 5,419,201 | 5/1995 | Li et al. | 324/71.1 X |
| 5,534,078 | 7/1996 | Breunsbach | 134/10 |

*Primary Examiner*—Michael Brock
*Attorney, Agent, or Firm*—Woodard, Emhardt, Naughton, Moriarty & McNett

[57] ABSTRACT

An apparatus and test method for determining the cleanliness (based on corrosivity) of a specific area on an electronic circuit assembly, such as the area between holes or pads on a single side of an assembly. The apparatus includes: (1) an extraction cell for providing an extraction fluid to an electronic circuit assembly ("ECA") area to be measured; (2) an extraction fluid for extracting residue from the ECA area to be measured; (3) a test cell with two or more electrodes and a voltage source for providing a voltage to the electrodes; and (4) a timer for measuring the time between the application of the voltage and an electrical short between the electrodes. The method includes: (1) positioning an extraction cell over an electronic circuit assembly area to be measured; (2) dispensing an extraction fluid into the extraction cell; (3) contacting the ECA area to be measured with the extraction fluid for a time sufficient to extract residue from the ECA area; (4) transferring the extraction fluid to a test cell made of two or more electrodes; (5) applying a voltage to the electrodes; and (6) measuring the time between the application of the voltage and an electrical short between the electrodes.

12 Claims, 6 Drawing Sheets

METHOD AND APPARATUS FOR THE QUANTITATIVE MEASUREMENT OF THE CORROSIVITY EFFECT OF RESIDUES PRESENT ON THE SURFACE OF ELECTRONIC CIRCUIT ASSEMBLIES

FIELD OF THE INVENTION

The present invention relates generally to a method and apparatus for measuring the cleanliness of electronic circuit assemblies.

BACKGROUND OF THE INVENTION

It is well know to the art that the cleanliness of an electronic assembly is critical to the assembly's field performance and reliability. Unfortunately, corrosive levels of ionic and nonionic residues may build up during the fabrication and assembly processes, and may also arise from external sources during field service. These residues frequently cause electrical shorting or corrosion failures to occur through electromigration or electrical leakage between two circuits.

Since passage of the Clean Air Act in 1987, many new and creative fabrication and assembly processes have emerged and are successfully being used to build hardware. In these modern methods the traditional use of chlorinated solvent cleaners has largely been discontinued, with aqueous, semi-aqueous or new nonchlorinated solvent cleaners now being preferred.

Modern electronic assembly methods are having greater field performance problems, particularly with respect to the contamination referred to above. For example, the new assembly methods which use no rosin or small amounts (<5%) of rosin do not have the protective insulative layer that traditional methods provided. Thus, the new processes are having failures due not to the materials used during assembly, but due to the normal fabrication and handling residues, or because the cleaning was only designed to remove the majority of the flux residue and not the layer of corrosive fabrication residues below the flux or beneath the components. These are new issues for the electronic assembly industry, because it was previously believed that solvent cleaning removed all fabrication and assembly corrosive residues instead of sealing them in with a clear thin layer of rosin.

Although research laboratory analytical tools such as ion chromatography (IC) and high pressure liquid chromatography (HPLC) may be used to separate, identify and quantify the ionic and nonionic residues present on electronic circuit assemblies, these are not production floor process control tools. The current inventive process control tools were developed for monitoring rosin flux and solvent cleaning residues, and are not capable of measuring the true cleanliness of an electronic assembly. Instead, current process control tools are merely gross performance indicators (trend tools) of the processing equipment. With these trend tools, less than 30% of the residues comes into solution during extraction, and generally a layer of flux residue, as well as fabrication residue, remains below this layer.

More particularly describing the prior art methods, most prior art trend tools use a solvent water (75% isopropyl alcohol and 25% water) extraction for 5–15 minutes at room temperature or at a slightly elevated temperature (limitation due to flammability), followed by measuring the total change in the conductivity of the solution over the time of the test. The resulting conductivity change is then compared to a conductivity salt standard (e.g., sodium chloride at about 750 ppm). There is no differentiation between corrosive and non-corrosive residues.

One further disadvantage of the prior art methods is that they are designed to extract whole- or half-board areas, and then to normalize the data to provide per unit area calculations (so much NaCl equivalents per square inch). Thus, the prior art methods are not effective for performing comparative cleanliness analysis (for corrosive residues) of various processing step effects, such as: (1) wave solder area vs. surface mount area; (2) top of board after wave solder vs. bottom of board; (3) bare incoming vs. assembled areas; (4) reworked areas vs. non-reworked areas, etc.

It can be seen from the above that the prior art does not provide a method for the simple, quantitative measurement of the corrosivity of an ionic and/or nonionic residues present on a specific area of an electronic circuit assembly. Additionally, the art does not provide a nondestructive spot extractor for IC and HPLC analysis to determine the actual contamination levels in specific areas on the board. The present invention addresses these needs.

SUMMARY OF THE INVENTION

Briefly describing one aspect of the present invention, there is provided an apparatus and method for quantitatively measuring the corrosivity effect of residues present on the surface of an electronic circuit assembly. The apparatus preferably comprises: (1) an extraction cell for providing an extraction fluid to an electronic circuit assembly ("ECA") area to be measured; (2) an extraction fluid for extracting residue from the ECA area to be measured; (3) a test cell having two or more electrodes and a voltage source for providing a voltage to the electrodes; and (4) an event detector for measuring the time between the application of the voltage and an electrical short between the electrodes.

The method for quantitatively measuring the corrosivity effect of residues present on the surface of an electronic circuit assembly preferably comprises: (1) positioning and securing an extraction cell over an electronic circuit assembly area to be measured; (2) dispensing an extraction fluid into said extraction cell; (3) contacting the ECA area to be measured with said extraction fluid for a time sufficient to extract residue from the ECA area; (4) providing the residue-containing extraction fluid to a test cell comprising two or more electrodes; (5) applying a voltage to at least one of the electrodes; and (6) measuring the time between the application of the voltage and an electrical short between the electrodes. After measuring the time between the application of the voltage and an electrical short between the electrodes (also called the time-to-migration, or "TM") a calculation of the amount of corrosive residue at the area being measured may be determined by comparison with test standards.

One object of the present invention is to provide a simple method and apparatus for the quantitative measurement of the corrosivity of a ionic and/or nonionic residues present on a specific area of an electronic circuit assembly.

Related objects and advantages of the present invention will be apparent from the following description.

DESCRIPTION OF THE PREFERRED EMBODIMENT

For the purposes of promoting an understanding of the principles of the invention, reference will now be made to preferred embodiments and specific language will be used to describe the same. It will nevertheless be understood that no limitation of the scope of the invention is thereby intended, such alterations and further modifications in the illustrated device, and such further applications of the principles of the invention as illustrated therein, being contemplated as would normally occur to one skilled in the art to which the invention relates.

As indicated above, the present invention provides an apparatus and method for quantitatively measuring the corrosivity effect of residues present on the surface of an electronic circuit assembly. The apparatus and test method are used as a process control tool, during the fabrication and assembly of electronic hardware, to measure the corrosivity (electromigration) effect of the residues removed from a specific area on the hardware surface.

Generally, the apparatus uses a small volume of a heated extraction solution on the area of the hardware surface (less than a square inch) and transfers that to a sacrificial electrode to measure the Time to Migration (TM) when the electrical short between the anode and cathode occurs. The results are compared to the solution standard and to previous data.

More particularly, the preferred apparatus comprises: (1) an extraction cell for providing an extraction fluid to an electronic circuit assembly ("ECA") area to be measured; (2) an extraction fluid for extracting residue from the ECA area to be measured; (3) a test cell having two or more electrodes and means for providing a voltage to at least one of the electrodes; and (4) means for measuring the time between the application of the voltage and an electrical short between the electrodes.

One preferred method comprises: (1) positioning the extraction cell over an electronic circuit assembly area to be measured; (2) dispensing the extraction fluid into the extraction cell so that the extraction fluid contacts the ECA area to be measured; (3) keeping the extraction fluid in contact with the ECA area to be measured for a time sufficient to extract residue from the ECA area and thus create a residue-containing extraction fluid; (4) transferring the residue-containing extraction fluid to a test cell comprising two or more electrodes; (5) applying a voltage to at least one of the electrodes; (6) measuring the time between the application of the voltage and an electrical short between the electrodes; and (7) using the time-to-migration numbers as an indicator of the amount of corrosive residue in the residue-containing extraction fluid. The faster the time-to-migration number, the higher the level of corrosive residues present in solution from the extraction.

Figure 1:
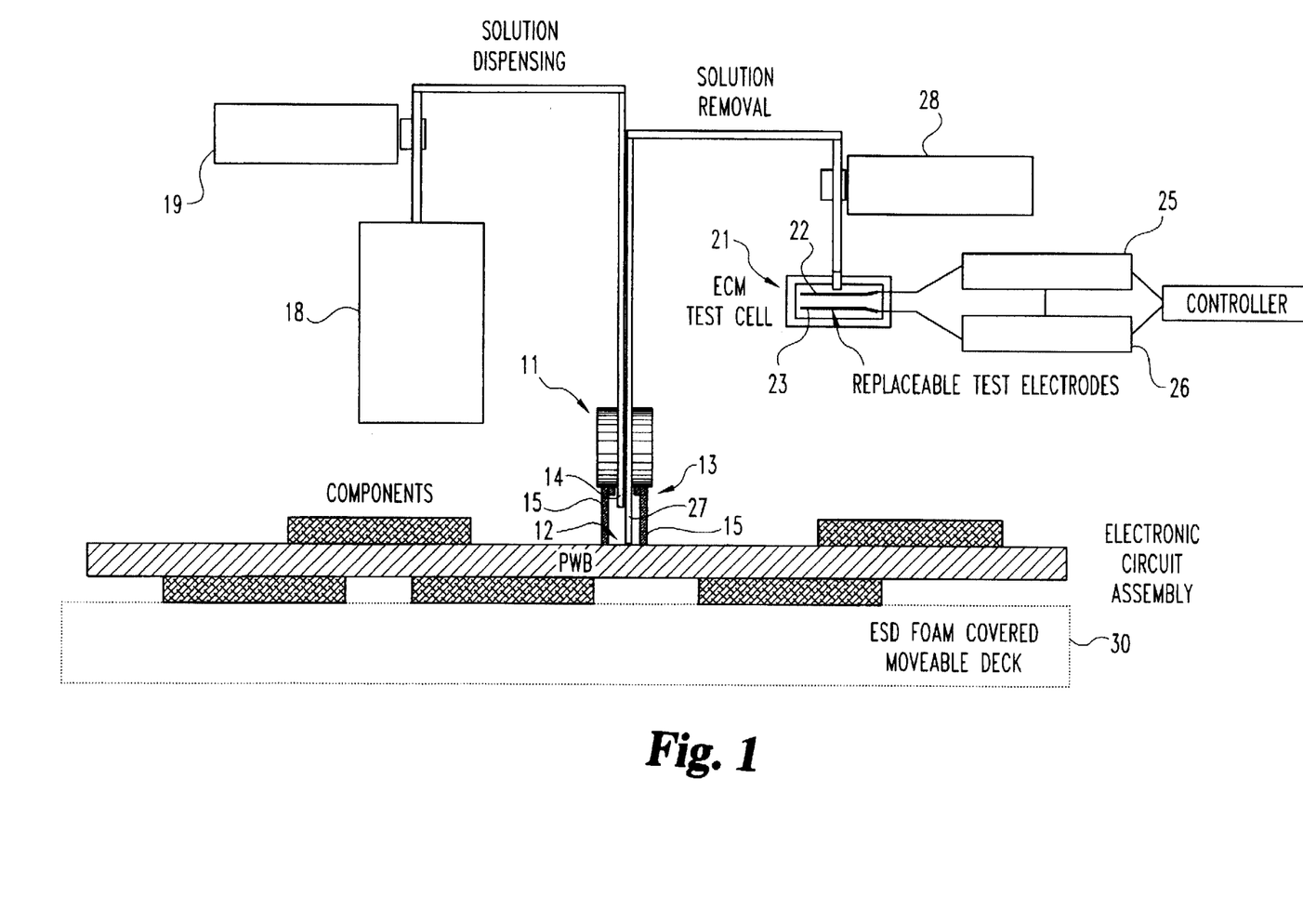
FIG. 1 shows the apparatus of the present invention, according to one preferred embodiment.

Describing the preferred embodiments in more detail, and with reference to the drawing, the preferred apparatus comprises an extraction cell 11 for providing extraction fluid to the ECA area to be measured 12, and for holding the fluid in contact with the ECA surface while extraction is accomplished. Extraction cell 11 preferably comprises an extraction head 13, having a fluid inlet/aspiration point 14 for providing extraction fluid to the interior of the extraction head, and a retainer ring 15 to hold the extraction fluid in a defined area and in contact with the electronic circuit assembly.

In one preferred embodiment, a solution dispensing system is used to provide the extraction fluid to extraction cell 11. The solution dispensing system preferably comprises a reservoir 18 to hold the extraction fluid, and a pump 19 for transferring extraction fluid from the reservoir to the extraction cell. A heater (not shown) may also be provided to heat the extraction fluid before use.

As discussed above, the preferred apparatus also includes a test cell 21 for measuring the corrosivity of the ECA area by measuring the time needed for the extracted residue to bridge the gap between the anode and the cathode, and thus to short the test cell during the applied current. Test cell 21 preferably comprises an interconnect slot and a housing to hold an electrode board. The electrode board is comprised of at least one pair of anodes and cathodes parallel to each at a specified spacing. A voltage source 25 is used to provide a current to the test cell, and an event detector 26 is used to measure the current flow across the electrodes. A fluid transfer line 27 provides the residue-containing extraction fluid to test cell 21, preferably by using a second fluid pump 28 to transfer the fluid.

A timer (not shown) is preferably used to measure the time to the migration event, i.e., the time until the residue causes the metal to migrate, bridging the gap and shortening the circuit between the two electrodes. A process controller may be used to control the timing of the apparatus, including the timing of solution dispensing and removal, as well as the timing of the voltage application and the migration event.

The electrodes are each preferably about 2–3 cm long and 20 mils thick, and are preferably spaced about 50 mils apart. In one preferred embodiment the electrodes made of copper or copper/laminate, as is known to the art for other electrodes. Smaller, larger or different metal electrodes and spacings may, of course, be used, although it should be recognized that this will have an effect on the base time-to-migration.

The amount of extraction fluid used in the method is typically about 0.2–0.7 ml, with 0.5 ml being most preferred. The fluid is preferably heated to a temperature of between about 120° F. and about 160° F., with the preferred temperature being about 140° F. As will be appreciated by those skilled in the art, smaller or greater amounts may be used depending on the specific items being tested. Similarly, cooler or warmer extraction temperatures may be used if the extraction fluid effectively extracts the residues to be measured from the ECA surface at such temperatures.

To hold the electronic circuit assembly while the measurement is performed, a deck 30 is preferably used. Further, a lock-down mechanism may be used to hold the electronic circuit assembly in place on the deck.

As to the preferred method, a fresh or properly cleaned retainer ring is first placed on the extraction head so that no contamination from the retainer ring can occur. An electronic circuit assembly (e.g., a circuit board) is then placed on the moveable deck. A test area is determined and the deck is locked into place. The extraction cell is lowered into place and locked in. The extraction solution is dispensed into the cell through the dispensing system, and the extraction solution is held in contact with the board surface for approximately 5–7 minutes. During this extraction time, the solution is preferably aspirated on and off and on the board surface at least several times. After extraction, the solution is provided to the test cell so that the residue-containing extraction fluid contacts the test electrodes. A voltage is applied to the electrodes, and a timer is started to measure the time to migration event (electrical short between of the electrode).

In one preferred embodiment, the solution is provided to contact the ECA area to be measured for about 2–5 minutes. In other embodiments extraction times of between 1 and 10 minutes are used. Shorter or longer extraction times may be used, depending largely on the rate at which the selected extraction fluid extracts the residue to be measured.

A voltage of between 2.0 volts and 10.0 volts is preferably used, with 3.5 volts being most preferred in applications tested to date. The voltage is applied for as long as it takes to create a short between the electrodes, commonly between about 3 and about 8 minutes.

As to the extraction fluid, the most preferred fluid is saponified deionized water. More generally, the preferred extraction solution is one which will solubilize the flux and assembly residues, as well as to penetrate the porous surface of a standard ECA. This porous surface of an ECA contains many corrosive and hydroscopic residues from the board fabrication process steps, and these residues are trapped in the exposed board laminate and soldermask areas. Preferred extraction fluids are therefore formulated to solubilize the new flux residues, activators and fabrication residues, and not to totally solubilize the organic solids of a traditional high solids rosin flux.

Further as to the extraction fluid, to accurately measure only the corrosivity effects of the residues removed from the surface of an ECA it is necessary to have an ionically clean solution to begin with. Accordingly, about 99% of the solution should be deionized (DI) water, with less than 0.01 parts per million (PPM) of corrosive residues (chloride, sulfate, and bromide) being present in that portion of the solution. Further, the DI water should have a solution resistance of about 17.5–18.3 meg ohms to achieve the appropriate level of cleanliness. The DI water is now an ionically hungry and becomes a polar solution.

In one preferred embodiment the extraction fluid also includes up to about 5% of a saponifier. The saponifier is preferably a monethanolamine (MEA) which contains nonionic surfactants to provide a low surface tension to the solution. MEA thus gives the solution its loading and solubilization strength. MEA is an EPA preferred chemical (see EPA document 743-B-96-001 "Aqueous and Semi-Aqueous Solvent Chemicals: Environmentally Preferable Choices", September, 1996).

It is to be appreciated that the components that contact the extraction fluid may be disposable, particularly the retainer tips and electrodes. The fluid is preferably transferred through Tygon® or similar tubing, so that contamination and cell wall degradation is minimized or eliminated.

Figure 2:
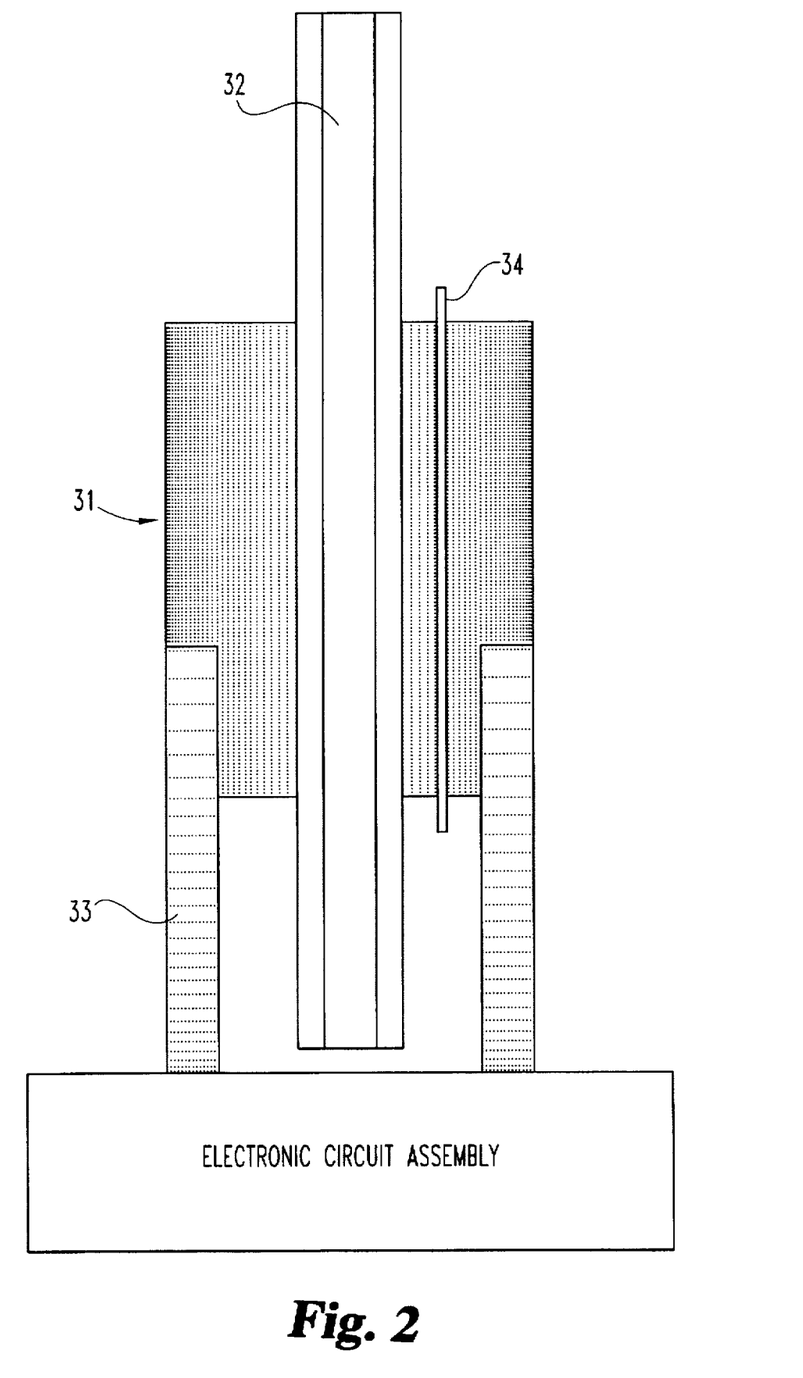
FIG. 2 shows the apparatus of the present invention, according to a second preferred embodiment.

In one embodiment, the extraction cell and the test cell use a solution delivery and aspiration system to provide extraction fluid to the ECA area to be measured, and to thereafter provide the extracted fluid to the test cell. Preferably, the solution delivery and aspiration system also facilitates recirculating the extraction fluid on and off of the board at least several, and preferably many, times during extraction. Accordingly, as shown in FIG. 2, one embodiment includes a test head 31 having a solution delivery and aspiration system 32 and a retainer tip 33. One or more vent tubes 34 may be provided, or the test head may be vented by leaving a space around the solution delivery and aspiration system, or by other means such as vent holes, etc.

In another preferred embodiment, the extraction cell and the test cell are combined into one extraction/test cell, preferably contained in a disposable tip. In this embodiment as in those previously described, the combined assembly may also include a filter effective for filtering the residues to be measured from the extraction fluid so that the fluid may be concentrated in its residue level.

Figure 3:
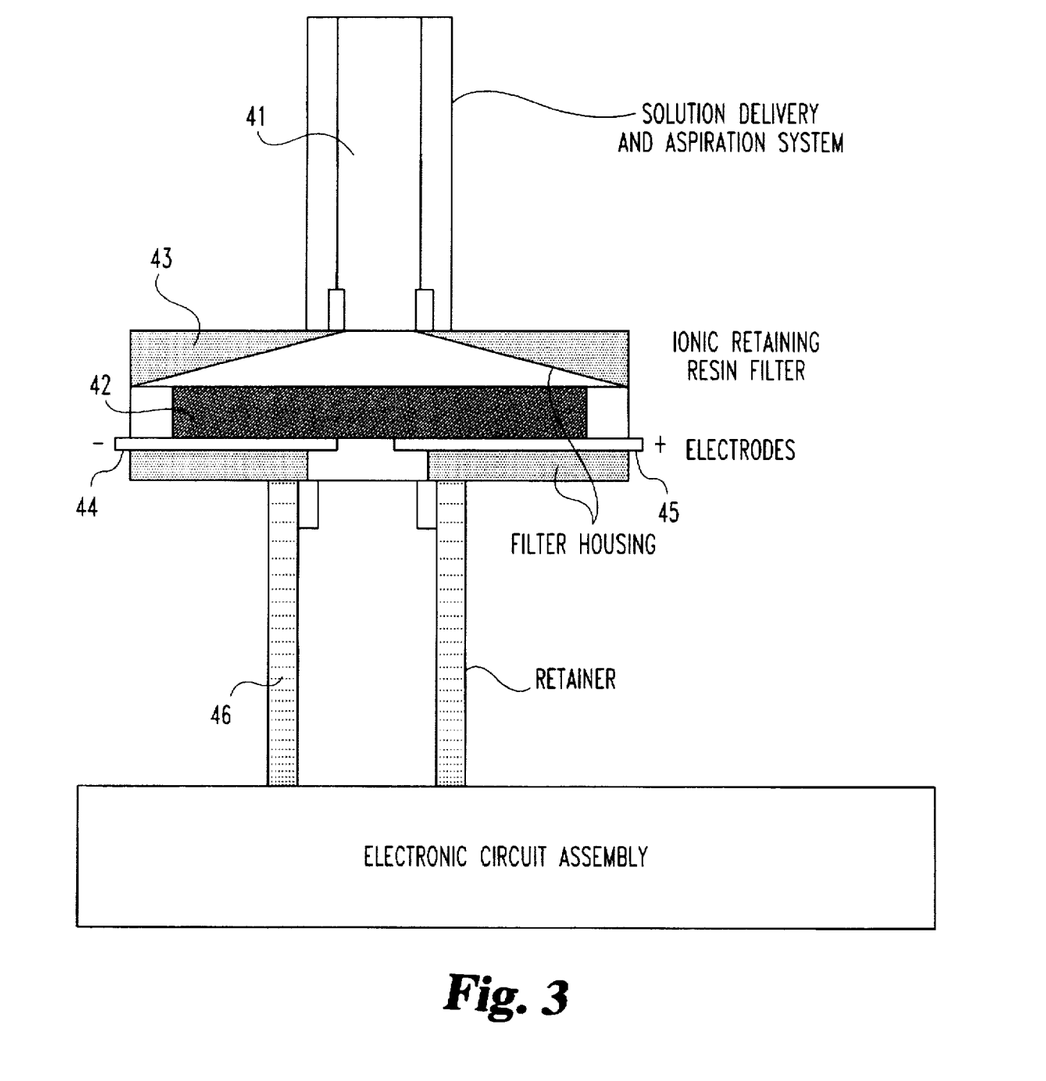
FIG. 3 shows the apparatus of the present invention, according to a third preferred embodiment, wherein the extraction cell and the test cell are combined into one extraction/test assembly.

Accordingly, as seen in FIG. 3, a combined extraction/test cell assembly preferably includes a solution delivery and aspiration system 41, an ionic retaining resin filter 42, a filter housing 43, electrodes 44 and 45, and a retainer tip 46. The electrodes are connected to a voltage source and an event detector (not shown) as previously described.

Figure 4:
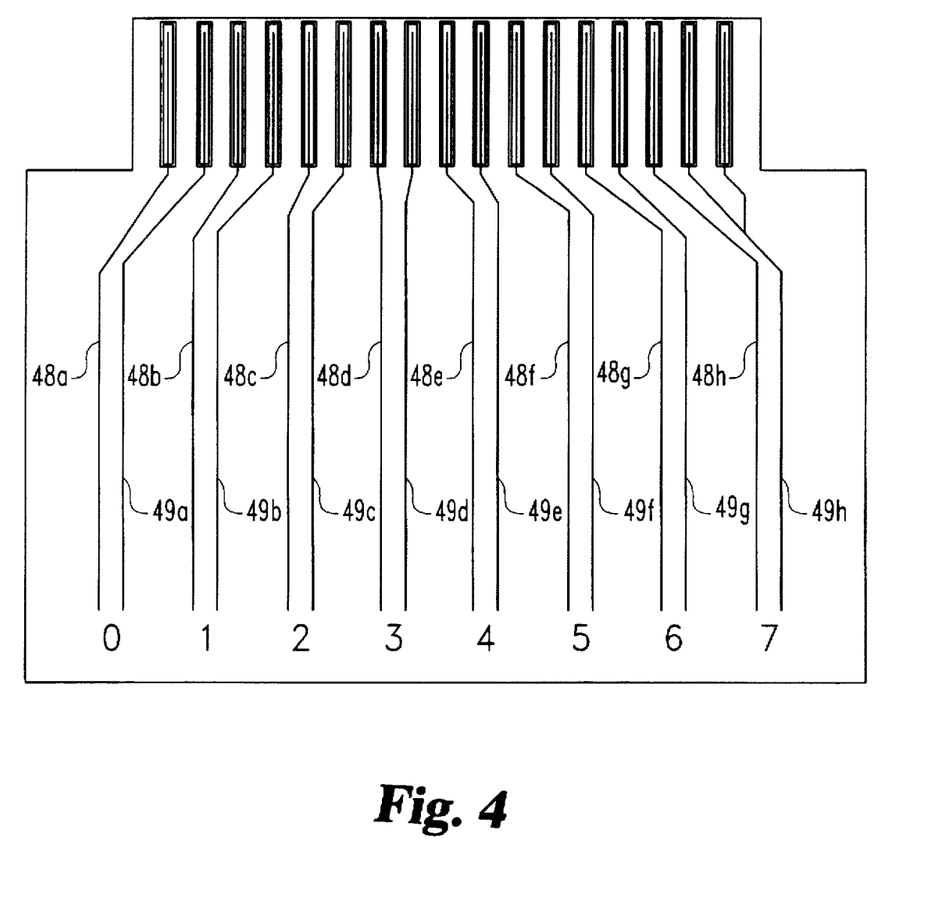
FIG. 4 shows a test cell electrode assembly, according to one preferred embodiment of the present invention.

It is also to be appreciated that the test cell may include more than one pair of electrodes so that multiple areas of an ECA may be tested simultaneously, or so that one area of the ECA may be tested with more than one measurement to provide a statistically-averaged value of the residue level on that area. In one such embodiment the test cell includes multiple electrodes 48a–h and 49a–h as shown in FIG. 4.

Finally, it is to be appreciated that the apparatus of the present invention may be used as an extraction tool only, with the analysis being performed by sophisticated analytical methods such as IC, HPLC, etc. In this embodiment, only the extraction cell, with an extraction fluid delivery and removal system, is preferably included.

In the "extraction cell only" embodiment the apparatus is used to extract the corrosive residue and to provide it to a separate analytical tool so that the extraction solution may be analyzed to quantify the different ionic species and levels present in solution. Accordingly, this embodiment of the invention provides a spot extractor for analytical tools such as ion chromatography, HPLC, ICAP, GC-mass spec, CES, and SEM/EDX. Persons skilled in the art appreciate how such tools may be integrated into the present invention to provide even more sensitive analysis than the basic test cell embodiment can provide. Persons skilled in the art can also appreciate how standards may be developed and used to calibrate the equipment, and to convert time-to-migration values to corrosive residue levels for the areas being measured.

Reference will now be made to specific examples using the processes described above. It is to be understood that the examples are provided to more completely describe preferred embodiments, and that no limitation to the scope of the invention is intended thereby.

EXAMPLE 1

An electronic circuit assembly is positioned and secured on a support deck. An extraction cell is positioned over an area of the ECA to be measured, and the cell is locked into place. A saponified solution of water is recirculated on and off of the area to be measured for about 2 minutes. After extraction, the residue-containing solution is provided to the space between the electrodes of a test cell and a voltage of about 3.5 volts is applied. A timer is started and the time-to-migration (the time to short the cell) is measured. The resulting time-to-migration is compared to time-to-migration times for known contamination levels to determine the contamination level of the ECA being measured. For example, chloride levels on a board of 28.8 mg/in$^2$ have a time-to-migration of 9 seconds using 5 volts, where a chloride level of 1.3 mg/in$^2$ has a time-to-migration of 88 seconds. (Chloride analysis of boards per standard IPC TM-6540.2.3.28 Ion chromatography test method.)

EXAMPLES 2 AND 3

Assemblies comprising bare copper boards are positioned and secured on a support deck. For each test, an extraction cell is positioned over the area to be measured, and the cell is locked into place. A saponified solution of water is recirculated on and off of the area to be measured for about 2 minutes. After extraction, the residue-containing solution is provided to the space between the electrodes of a test cell and a voltage of about 5 volts is applied. A timer is started and the time-to-migration (the time to short the cell) is measured. The resulting time-to-migration is compared to time-to-migration times for known contamination levels to determine the contamination level of the ECA being measured. The results are shown in FIG. 5.

Figure 5:
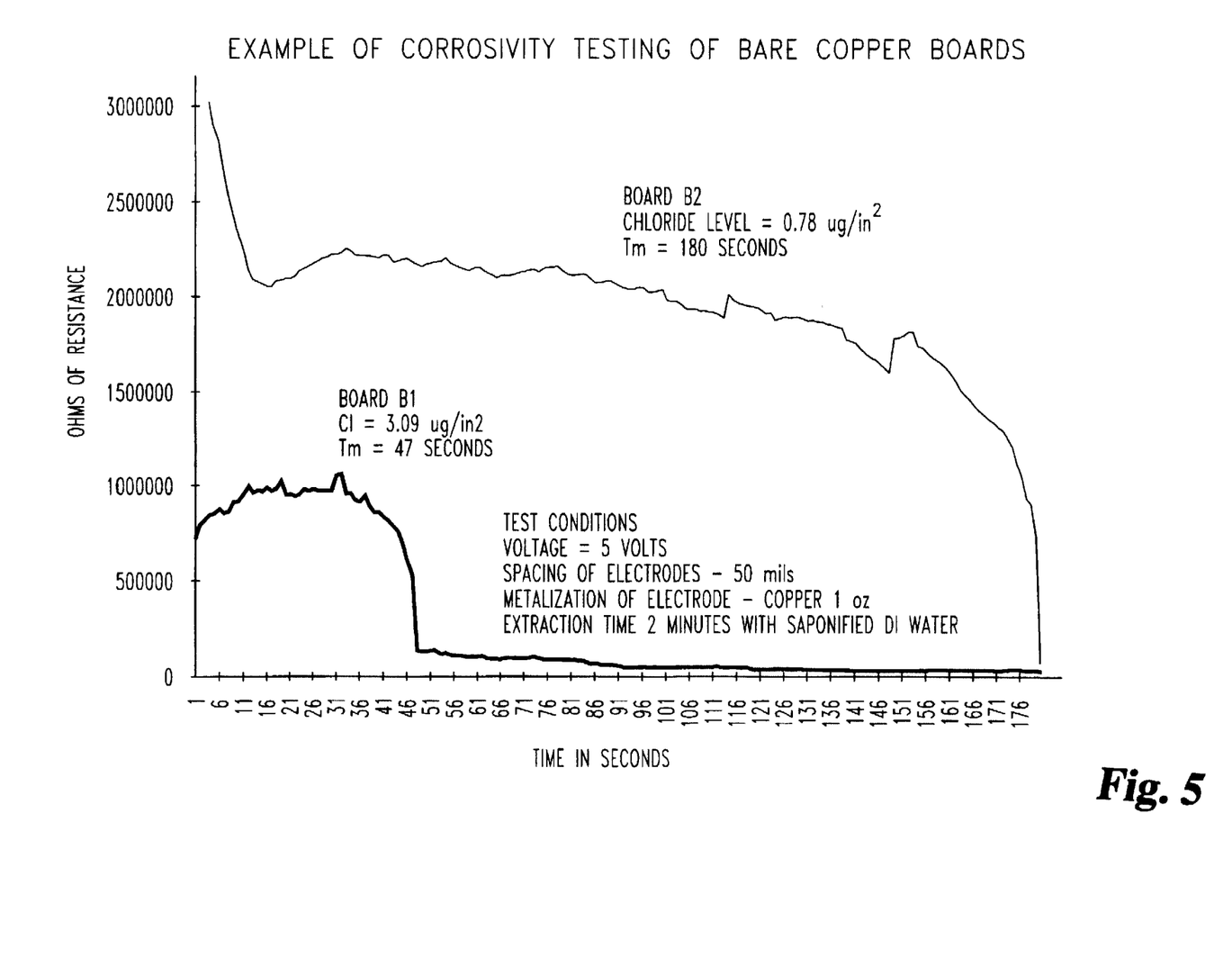
FIG. 5 is a graph showing the results of corrosivity testing of bare copper boards.

FIG. 5 is a line xy graph with the x axis of time in seconds and a y axis of electrical resistance between to metal traces on FR-4 laminate measured in ohms under a drop of extraction solution. Line 1 (the heavy weighted line) shows a line that indicates the resistance change during the test time of 3 minutes under the 5 volt bias for the electrode (with a spacing of 50 mils between and a drop of extraction solution that had been exposed to two minutes on a bare unprocessed board. Then the board was tested per the IPC TM 650 2.3.28 method of ionic analysis by Ion Chromatography and the level of chloride was determined. The resistance starts at 750,000 ohms of between the two traces and rises to 1,000,000 ohms then drops to <10,000 ohms at the 48 second mark and stays below this. This drop in resistance between the two electrodes indicates the formation of a copper bridge between the two electrodes. This drop in resistance is an electrical short.

Line 2 (the weighted line) shows a line that indicates the resistance change during the test time of 3 minutes under the 5 volt bias for the electrode (with a spacing of 50 mils between and a drop of extraction solution that had been exposed to two minutes on an unprocessed bare copper board. Then board was tested per the IPC TM 650 2.3.28 method of ionic analysis by Ion Chromatography and the level of chloride was determined. The resistance starts at >3,000,000 ohms of between the two traces and stabilizes out to 2,000,000 ohms then drops to <10,000 ohms at the 180 second mark and stays below this. This drop in resistance between the two electrode indicates the formation of a copper bridge between the two electrodes. This drop in resistance is an electrical short. The base extraction solution will cause an electrical short at ~320 seconds.

The interpretation of the two test runs is that the shorter the time-to-migration means that there is more corrosive residue in the extraction solution from one board than the other board. We see that there is a big difference in the amount of chloride present on one board vs. the other. This can be seen by the high level of chloride shown by Ion Chromatography on the dirty board and the low level shown on the clean board.

Electrical shorts between the electrodes will occur under the extraction solution, but if all the variables are kept constant (electrode metalization, spacing, board material, voltage starting extraction solution and starting board cleanliness of the electrode) and only allowed the cleanliness of the extraction solution to change through whatever contaminants were removed from the board surface, then a comparison can be made as to the cleanliness of the bare board extracted. Short time-to-migration is an indication that there were large amounts of corrosive contaminants removed from the surface of the assembly that caused the electrical short to occur faster. Long time-to-migrations would indicate that low levels of corrosive contaminants were present in the extraction solution and take a longer time to cause a short.

EXAMPLES 4 AND 5

Figure 6:
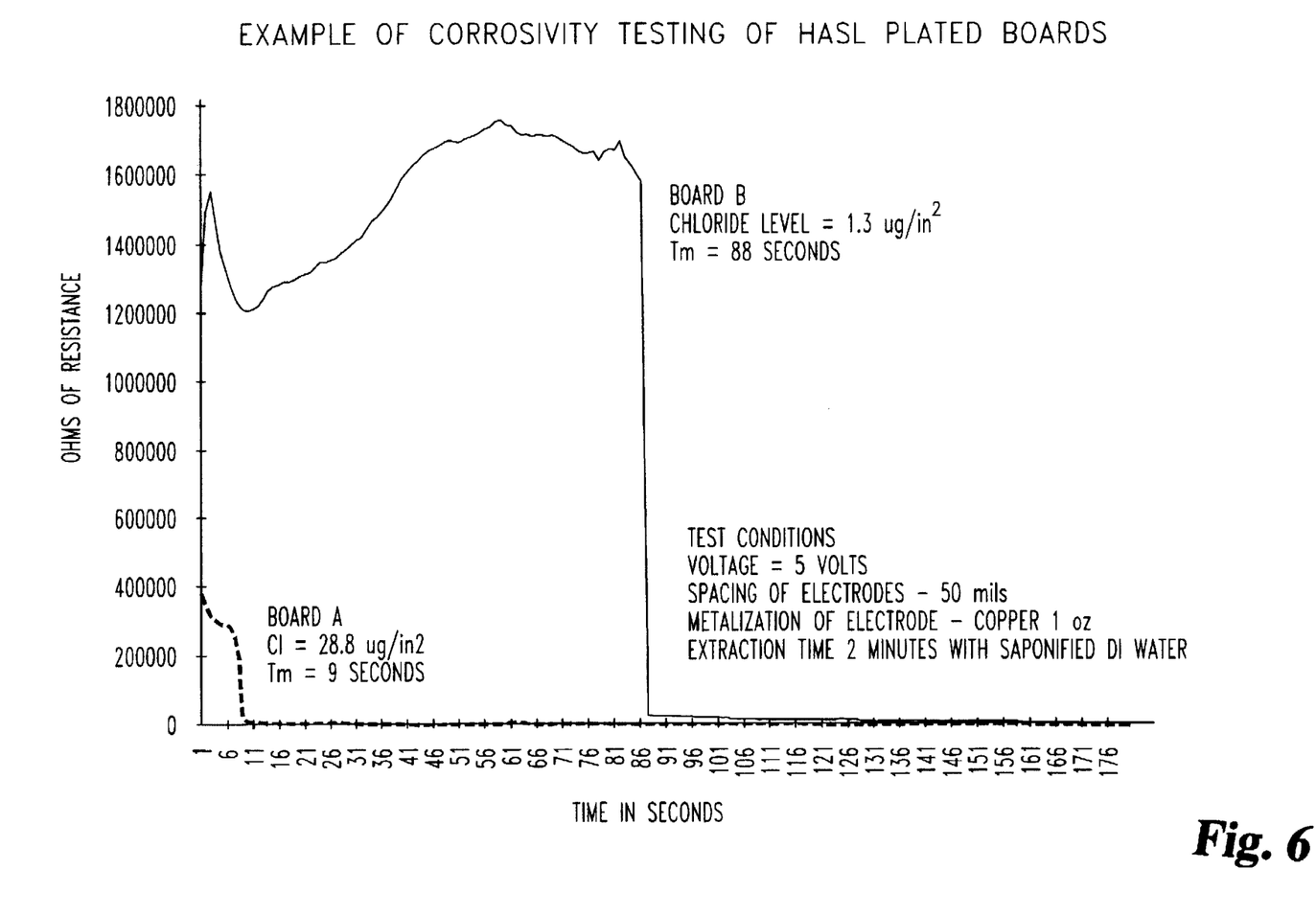
FIG. 6 is a graph showing the results of corrosivity testing of HASL-plated boards.

Assemblies comprising bare copper boards are positioned and secured on a support deck. For each test, an extraction cell is positioned over the area to be measured, and the cell is locked into place. A saponified solution of water is recirculated on and off of the area to be measured for about 2 minutes. After extraction, the residue-containing solution is provided to the space between the electrodes of a test cell and a voltage of about 5 volts is applied. A timer is started and the time-to-migration (the time to short the cell) is measured. The resulting time-to-migration is compared to time-to-migration times for known contamination levels to determine the contamination level of the ECA being measured. The results are shown in FIG. 6.

Examples 4 and 5 are similar to examples 2 and 3 above, but the bare boards which were extracted were hot air solder leveled ("HASLed") and not just bare copper. Ion Chromatography analysis of the boards show that one board was high in chloride and one board was low. The time-to-migration for the dirty board was much short (<10 seconds) as compared to the 88 seconds of the clean board.

While the invention has been illustrated and described in detail in the drawings and foregoing description, the same are to be considered as illustrative and not restrictive in character, it being understood that only the preferred embodiment has been shown and described and that all changes and modifications that come within he spirit of the invention are desired to be protected.

What is claimed is:

1. A method for quantitatively measuring the corrosivity effect of residues present on the surface of an electronic circuit assembly, the method comprising:
   a. positioning an extraction cell over an electronic circuit assembly ("ECA") area to be measured;
   b. dispensing an extraction fluid into said extraction cell;
   c. contacting the ECA area to be measured with said extraction fluid for a time sufficient to extract residue from the ECA area and create a residue-containing fluid;
   d. providing said residue-containing fluid to a test cell comprising two or more electrodes, wherein the residue-containing fluid is provided at least to the space between the electrodes;
   e. applying a voltage to at least one of the electrodes;
   f. measuring the time between the application of the voltage and an electrical short between the electrodes.

2. The method of claim 1 and further including the step of converting the measured time between the application of the voltage and an electrical short between the electrodes to a value for the amount of residue extracted from the assembly.

3. The method of claim 1 wherein said extraction cell and said test cell are combined into one extraction/test cell.

4. The method of claim 1 wherein said extraction fluid is allowed to contact said ECA area for a time of between two minutes and ten minutes.

5. The method of claim 1 wherein said voltage is between 1.0v and 5.0v.

6. The method of claim 1 wherein said voltage is between 3.0v and 4.0v.

7. The method of claim 1 wherein said extraction fluid is a saponified deionized water.

8. An apparatus for quantitatively measuring the corrosivity effect of residues present on the surface of an electronic circuit assembly, the apparatus comprising:

(a) an extraction cell for providing an extraction fluid to an electronic circuit assembly ("ECA") area to be measured;

(b) an extraction fluid for extracting residue from the ECA area to be measured;

(c) a test cell having a first electrode and a second electrode; said test cell further having means for providing a voltage to said first electrode; and (d) means for measuring the time between the application of the voltage and an electrical short between the electrodes.

9. The apparatus of claim 8 wherein said extraction cell and said test cell are combined into one extraction/test assembly.

10. The apparatus of claim 8, and further including a filter to retain extracted residue and thereby concentrate the residue-containing extraction fluid.

11. The apparatus of claim 8 wherein said extraction fluid is a saponified deionized water.

12. A method for quantitatively measuring the corrosivity effect of residues present on the surface of an electronic circuit assembly, the method comprising:

a. positioning an extraction cell over an electronic circuit assembly ("ECA") area to be measured;

b. dispensing a non-ionic extraction fluid into said extraction cell;

c. contacting the ECA area to be measured with said extraction fluid for a time sufficient to extract residue from the ECA area and create a residue-containing fluid;

d. providing said residue-containing fluid to a test apparatus for measuring the residue levels present in the residue-containing fluid; and e. using the test apparatus to measure the residue levels present in the residue-containing fluid.

* * * * *